US006169199B1

(12) United States Patent
Rehfinger et al.

(10) Patent No.: US 6,169,199 B1
(45) Date of Patent: Jan. 2, 2001

(54) METHOD FOR SEPARATING 6-AMINOCAPROIC ACID NITRILE FROM MIXTURES CONTAINING 6-AMINOCAPROIC ACID NITRILE AND AN IMINE

(75) Inventors: Alwin Rehfinger, Mutterstadt; Hermann Luyken, Ludwigshafen, both of (DE)

(73) Assignee: BASF Aktiengesellschaft, Ludwigshafen (DE)

( * ) Notice: Under 35 U.S.C. 154(b), the term of this patent shall be extended for 0 days.

(21) Appl. No.: 09/367,068

(22) PCT Filed: Jan. 30, 1998

(86) PCT No.: PCT/EP98/00505

§ 371 Date: Aug. 9, 1999

§ 102(e) Date: Aug. 9, 1999

(87) PCT Pub. No.: WO98/34912

PCT Pub. Date: Aug. 13, 1998

(30) Foreign Application Priority Data

Feb. 7, 1997 (DE) .............................................. 197 04 613

(51) Int. Cl.$^7$ ................................................. C07C 255/00

(52) U.S. Cl. ............................................................ 558/452

(58) Field of Search ................................ 558/452; 203/94

(56) References Cited

U.S. PATENT DOCUMENTS

| 4,389,348 | 6/1983 | Diamond et al. | 260/465 |
| 4,601,859 | 7/1986 | Galle et al. | 558/459 |
| 5,133,838 | 7/1992 | Sieja | 203/29 |
| 5,153,351 | 10/1992 | Sieja | 558/452 |
| 5,162,567 | 11/1992 | Sieja | 558/452 |
| 5,192,399 | 3/1993 | Sieja | 203/36 |

FOREIGN PATENT DOCUMENTS

| 4235466 | 4/1994 | (DE) . |
| 19500222 | 7/1996 | (DE) . |
| 19548289 | 6/1997 | (DE) . |
| 077911 | 5/1983 | (EP) . |
| 161419 | 11/1985 | (EP) . |
| 497333 | 8/1992 | (EP) . |
| 628025 | 12/1994 | (EP) . |
| 93/01207 | 1/1993 | (WO) . |

OTHER PUBLICATIONS

Kirk–Othmer Enc. of Chem. Tech., vol. 7, 1979, 870–881.

*Primary Examiner*—Cecilia Tsang
*Assistant Examiner*—Joseph Murray
(74) *Attorney, Agent, or Firm*—Keil & Weinkauf

(57) ABSTRACT

A process for distillative removal of 6-aminocapronitrile from mixtures (I) comprising 6-aminocapronitrile and an imine (II) comprises performing the distillation in a distillation column using an average mean residence time for the distillation mixture of at least 5 minutes on at least one level of the distillation column.

6 Claims, No Drawings

METHOD FOR SEPARATING 6-AMINOCAPROIC ACID NITRILE FROM MIXTURES CONTAINING 6-AMINOCAPROIC ACID NITRILE AND AN IMINE

This application is a 371 of PCT/EP98/00505 filed Jan. 30, 1998.

DESCRIPTION

The present invention relates to a process for distillative removal of 6-aminocapronitrile from mixtures (I) comprising 6-aminocapronitrile and an imine (II).

The partial hydrogenation of aminonitrile to 6-aminocapronitrile in the presence of a catalyst based on a metal such as nickel, cobalt, iron, rhodium or ruthenium is generally known, for example from EP-A-161 419, EP-A-77 911, U.S. Pat. No. 4,389,348, U.S. Pat. No. 4,601,859, WO 93/1207, DE-A 42 35 466, DE-A 19 500 222 and German Application 19 548 289.1.

Byproducts include imines, especially tetrahydroazepine of the formula

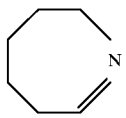

6-Aminocapronitrile is chiefly used for fiber production via caprolactam as intermediate or by direct polymerization to nylon-6. For this, the 6-aminocapronitrile has to be very pure, in which connection it is known that the removal of tetrahydroazepine presents problems.

U.S. Pat. No. 5,162,567 discloses reacting a mixture comprising 6-aminocapronitrile and tetrahydroazepine with an organic carbonyl compound, for example with a ketone or an aldehyde, at high temperature and then removing 6-aminocapronitrile from the mixture. U.S. Pat. No. 5,153,351 discloses reacting a mixture comprising 6-aminocapronitrile and tetrahydroazepine with an organic active-CH methylene compound, for example malonitrile, cyclopentadiene, nitromethane or nitroethane, and then removing 6-aminocapronitrile from the mixture.

The disadvantage for these processes is that the addition of a further organic compound to the mixture makes it more difficult to prepare pure 6-aminocapronitrile.

In U.S. Pat. No. 5,133,838, a mixture comprising 6-aminocapronitrile and tetrahydroazepine is reacted with an inorganic hydride such as lithium borohydride. Disadvantageously, in this process, the hydride has to be used in a multiple excess of the stoichiometrically required quantity. In addition, care has to be taken in the subsequent distillation not to hydrogenate the 6-aminocapronitrile.

EP-A-497 333 describes a process whereby a mixture comprising 6-aminocapronitrile and tetrahydroazepine is reacted with an alkaline compound. Disadvantageously, the alkaline compound has to be used in excess over the stoichiometrically required quantity and the 6-aminocapronitrile has to be distilled out of the resulting reaction mixture at greatly reduced pressure.

EP-A-628 025 discloses heating mixtures comprising 6-aminocapronitrile and tetrahydroazepine to 235° C. prior to the distillation in order that tetrahydroazepine may be converted into compounds which can be removed from 6-aminocapronitrile by distillation.

It is an object of the present invention to provide a technically simple and economical process for removing 6-aminocapronitrile from a mixture comprising essentially 6-aminocapronitrile and tetrahydroazepine by overcoming the aforementioned disadvantages.

We have found this object is achieved by a process for distillative removal of 6-aminocapronitrile from mixtures (I) comprising 6-aminocapronitrile and an imine (II), which comprises performing the distillation in a distillation column using an average mean residence time for the distillation mixture of at least 5 minutes on at least one level of the distillation column.

Mixtures (I) are obtainable in a conventional manner by partial hydrogenation of adiponitrile, for example according to a process as described in EP-A-161 419, EP-A-77 911, U.S. Pat. No. 4,389,348, U.S. Pat. No. 4,601,859, WO 93/1207, DE-A 42 35 466, DE-A 19 500 222 and German Application 19 548 289.1, by, in general, conducting the hydrogenation in the presence of nickel-, cobalt-, iron-, rhodium- or ruthenium-containing catalysts. The catalysts can be used as supported or unsupported catalysts. Catalyst supports include for example aluminum oxide, silicon dioxide, titanium dioxide, magnesium oxide, activated carbons and spinels. Examples of unsupported catalysts are Raney nickel and Raney cobalt.

The hydrogenation affords a mixture comprising 6-aminocapronitrile, hexamethylenediamine an imine (II) with or without adiponitrile.

From this mixture it is possible to obtain a mixture (I) comprising essentially 6-aminocapronitrile and an imine (II), for example by distillation.

An imine (II) is suitably selected from aromatic, preferably aliphatic, such as acyclic or especially cyclic imines and also mixtures thereof, particularly preferably tetrahydroazepine.

Suitable distillation apparatus is any customary distillation column, as described for example in: Kirk-Othmer, Encyclopedia of Chemical Technology, 3rd ed., Vol. 7, John Wiley & Sons, New York, 1979, pages 870–881, such as sieve plate columns, bubble cap columns or columns packed with arranged or dumped packing.

Preference is given to distillation apparatus having a pressure drop from the bottom to the top within the range from 1 to 1000 mbar, preferably within the range from 3 to 300 mbar, for which the pressure should advantageously be within the range from 10 to 1000 mbar at the bottom and within the range from 30 to 300 mbar at the top.

The distillation can be carried out in a plurality of columns, such as 2 or 3 columns, but is preferably carried out in a single column.

According to the invention, the distillation mixture has an average mean residence time of at least 5 minutes, preferably at least 15 minutes, especially at least 45 minutes, on at least one, preferably from 1 to 15, particularly preferably from 1 to 7, especially 1, 2 or 3, levels of the distillation column.

It is preferable to withdraw the distillation mixture from the distillation column on at least one level, pass it through a delay vessel and return it into the distillation column. The returning can take place onto the withdrawal level or onto a level above or below the withdrawal level.

It is advantageous for the distillation column reflux to pass first through a delay vessel before it is returned into the distillation column.

The withdrawing of distillation liquid from the column, the passing through the delay vessel, the returning into the distillation column and, optionally, the recirculating of the liquid in the delay vessel may all be effected using conventional apparatus, such as a pump, in which case the returning may take place onto the withdrawal level of the distillation column, especially in the case of a plate column, or onto a level which is above, especially in the case of an arranged-packing column, or below the withdrawal level.

The distillation of mixture (I) can be carried out with advantage in the presence of carbon dioxide.

Carbon dioxide can be added to the distillation mixture before or preferably during the distillation in the form of a compound which releases carbon dioxide under the distillation conditions, such as ammonium carbonate, ammonium carbamate or urea or mixtures thereof, in which case these compounds can be added in pure form or in a liquid diluent, as in one or more constituents of mixture (I), or in the form of solid, liquid or preferably gaseous carbon dioxide, for example in the form of a gas comprising carbon dioxide, especially in the form of pure gaseous carbon dioxide which comprises only the customary impurities.

The carbon dioxide content of the distillation mixture should be within the range from 0.1 to 100 mol of carbon dioxide per mole of imine function of imine (II).

The distillation of mixture (I) can advantageously be effected by addition of a compound (III) which is inert to 6-aminocapronitrile under the distillation conditions and whose boiling point under the distillation conditions is above the boiling point of 6-aminocapronitrile.

Suitable compounds (III) include aromatics, aliphatics, such as cyclic and acyclic aliphatics, and aliphatic aromatics. These compounds can bear substituents, such as a hydroxyl, keto, ester, alkyl, aryl, cycloalkyl, arylalkyl group, preferably a nitro or amino group, or a plurality of identical or different such groups.

The compound (III) can consist of one compound or of mixtures of such compounds.

It is advantageous to use compounds (III) which are simple to convert, as by hydrogenation, for example with a gas comprising molecular hydrogen in the presence of a catalyst, into hexamethylenediamine, preferably 6-aminocapronitrile.

The products obtained in this reaction can advantageously be used afresh in the process of the invention.

The difference in the boiling points between the amine (I) and the compound (IV) should be within the range from 1 to 200° C., preferably within the range from 5 to 100° C., under the distillation conditions.

The use of adiponitrile or mixtures comprising essentially adiponitrile is particularly advantageous.

The compound (III) can be added to the mixture (I) before or during the distillation.

The addition of compound (III) to mixture (I) before the distillation can be effected in a conventional manner in customary mixing apparatus.

The addition of compound (III) to mixture (I) during the distillation can be effected by feeding the compound (III) into the distillation apparatus, preferably into the bottom region.

The process of the invention affords 6-aminocapronitrile as overhead product. If the mixture (I) includes adiponitrile, this can be removed especially via a sidestream take-off and be returned with advantage into the aforementioned complete or preferably partial hydrogenation.

EXAMPLES

In the Examples, all percentages are by weight, unless otherwise stated.

Comparative Example 275 g/h of a mixture comprising 0.061% of tetrahydroazepine, 0.27% of hexamethylenediamine and 48% of 6-aminocapronitrile (balance adiponitrile) were continuously fed into a column having a low pressure drop woven packing corresponding to 32 theoretical plates.

At the top of the column, a pressure of 14 mbar was set, a constant of 125 g/h of distillate withdrawn and a reflux of 87 g/h applied.

The overhead effluent collected over a period of 16 h under steady state conditions included 0.6% of hexamethylenediamine and 0.13% of tetrahydroazepine as well as 6-aminocapronitrile.

Inventive Example 1

The comparative example was repeated, except that, before being returned into the column, the reflux was passed through a delay vessel thermostatically controlled at 100° C. The residence time in the vessel was 30 min.

The overhead effluent collected over a period of 17 h under steady state conditions included 0.6% of hexamethylenediamine and 0.12% of tetrahydroazepine as well as 6-aminocapronitrile.

Inventive Example 2

The comparative example was repeated, except that the top 3 theoretical plates (woven packing) were exchanged for bubble cap plates having a liquid holdup of 45 ml/plate, resulting in a total residence time on these plates of 30 minutes.

The overhead effluent collected over a period of 17 h under steady state conditions included 0.6% of hexamethylenediamine and 0.11% of tetrahydroazepine as well as 6-aminocapronitrile.

Inventive Example 3

The comparative example was repeated, except that the top 6 theoretical plates (woven packing) were exchanged for bubble cap plates having a liquid holdup of 45 ml/plate, resulting in a total residence time on these plates of 30 minutes.

The overhead effluent collected over a period of 16 h under steady state conditions included 0.6% of hexamethylenediamine and 0.062% of tetrahydroazepine as well as 6-aminocapronitrile.

Inventive Example 4

The comparative example was repeated, except that the top 10 theoretical plates (woven packing) were exchanged for bubble cap plates having a liquid holdup of 45 ml/plate, resulting in a total residence time on these plates of 30 minutes.

The overhead effluent collected over a period of 16 h under steady state conditions included 0.6% of hexamethylenediamine and 0.013% of tetrahydroazepine as well as 6-aminocapronitrile.

We claim:
1. A process for distillative removal of 6-aminocapronitrile from mixtures (I) comprising 6-aminocapronitrile and an imine (II), which comprises performing the distillation in a distillation column using an average mean residence time for the distillation mixture of at least 5 minutes on at least one level of the distillation column.

2. A process as claimed in claim 1, wherein the distillation mixture is withdrawn from the column on at least one level, passed through a delay vessel and then returned into the column.

3. A process as claimed in claim 1, wherein the column reflux is first passed through a delay vessel before it is returned into the distillation column.

4. A process as claimed in claim 1, wherein a cyclic imine is used as imine (II).

5. A process as claimed in claim 1, wherein tetrahydroazepine is used as imine (II).

6. A process as claimed in claim 1, wherein the distillation is carried out within the range from 10 to 1000 mbar.

* * * * *